United States Patent [19]
Jackson

[11] 3,985,898
[45] Oct. 12, 1976

[54] THIOUREA DERIVATIVES
[75] Inventor: John Lambert Jackson, Exmouth, England
[73] Assignee: John Wyeth & Brother Limited, Maidenhead, England
[22] Filed: Apr. 29, 1975
[21] Appl. No.: 572,783

[30] Foreign Application Priority Data
May 17, 1974 United Kingdom............... 21980/74

[52] U.S. Cl............................. 424/322; 260/552 R; 260/553 R; 260/553 A
[51] Int. Cl.² ...................................... A61K 31/17
[58] Field of Search................. 424/322; 260/552 R, 260/553 R, 553 A

[56] References Cited
UNITED STATES PATENTS

| | | | |
|---|---|---|---|
| 2,870,161 | 1/1959 | Bloom | 424/322 |
| 2,983,646 | 5/1961 | Ruhoff | 424/322 |
| 3,748,356 | 7/1973 | Wellinga | 260/522 R |

OTHER PUBLICATIONS
Takahashi et al., *Chemical Abstracts* 59: 611c, (1962).
Takahashi et al., *Chemical Abstracts* 65:668e, (1966).

*Primary Examiner*—Norman A. Drezin

[57] ABSTRACT
Thioureas of the formula

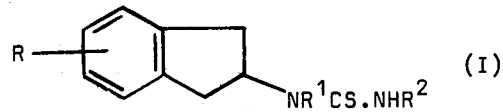

wherein R represents hydrogen, halogen, lower alkyl or lower alkoxy, $R^1$ represents hydrogen or lower alkyl and $R^2$ represents aroyl can be hydrolysed to compounds in which $R^2$ is hydrogen. The compounds in which $R^2$ is hydrogen exhibit anorectic activity.

5 Claims, No Drawings

THIOUREA DERIVATIVES

This invention relates to thiourea derivatives, to processes for preparing them and to pharmaceutical compositions containing certain of them.

The present invention provides thioureas of the general formula (I)

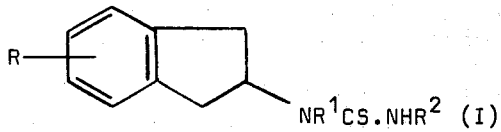

wherein R represents hydrogen, halogen, lower alkyl or lower alkoxy, $R^1$ represents hydrogen or lower alkyl and $R^2$ represents hydrogen or aroyl.

The term "lower" as used herein in relation to alkyl and alkoxy radicals means that the radicals contain from 1 to 6 carbon atoms. Preferably such radicals contain from 1 to 4 carbon atoms.

The group R is hydrogen, halogen (for example fluorine, chlorine or bromine), lower alkyl (for example methyl, ethyl, propyl or butyl) or lower alkoxy (for example methoxy, ethoxy, propoxy or butoxy). Preferably R is hydrogen, halogen or lower alkoxy and the most preferred meaning of R is hydrogen.

When $R^1$ is lower alkyl it can be, for example, methyl, ethyl, propyl or butyl. Preferably $R^1$ is hydrogen.

The compounds of general formula (I) in which $R^2$ is hydrogen exhibit anorectic activity upon administration to warm-blooded animals according to standard test procedures. In addition they exhibit anti-ulcer activity. The compounds of general formula (I) in which $R^2$ is aroyl are intermediates for preparing the compounds of general formula (I) in which $R^2$ is hydrogen. When $R^2$ is aroyl it may be for example a benzoyl radical. The phenyl group of the benzoyl radical is preferably unsubstituted but it may be substituted by, for example, lower alkyl, lower alkoxy, halogen and the like.

The compounds of general formula (I) in which $R^2$ is hydrogen may be prepared by hydrolysis of the compounds of general formula (I) in which $R^2$ is aroyl. The hydrolysis can, for example, be effected under basic conditions.

The compounds of general formula (I) in which $R^2$ is aroyl may be prepared by reacting an amine of general formula (II)

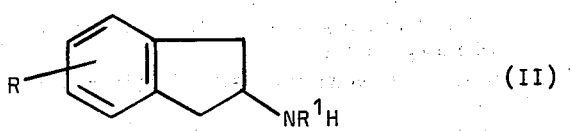

(wherein R and $R^1$ are as defined above) with an isothiocyanate of formula (III)

$$R^3NCS \qquad (III)$$

(where $R^3$ is aroyl). The amine can be reacted with the isothiocyanate by methods known per se. For example, the reactants may be heated together in a suitable solvent. The isothiocyanate of general formula (III) can be prepared by reacting a thiocyanate salt (e.g. ammonium thiocyanate) with an aroyl halide; the product need not be isolated from the reaction mixture but it can be reacted with the amine of general formula (II) in situ to yield the compound of general formula (I) where $R^2$ is an aroyl group.

The amines of general formula (II) and the isothiocyanates of formula (III) are known compounds or can be prepared by methods known in the art for preparing analogous compounds.

If necessary, in the reactions hereinbefore described, reactive substituent groups may be protected during a reaction and the protecting group removed at a later stage. Once the compound of general formula (I) has been prepared then if necessary a substituent in the molecule may be converted into another substituent within the meaning specified in connection with general formula (I).

As mentioned above, the compounds of general formula (I) in which $R^2$ is hydrogen exhibit anorectic activity. The compounds are tested for anorectic activity by the following procedure:

Groups of 8 or 10 male mice weighing 22–24 grams are starved overnight, although access to water is not restricted. The animals are dosed with the test drug or vehicle alone (control) one hour before they are placed individually into glass jars. The jars (100 mm. diameter × 80 mm. high) have lids fitted with a glass tube to accommodate a stick of spaghetti of approximate length of 450 mm. The glass tube is arranged such that only 5 mm. of spaghetti is exposed for eating by the mouse. The length of spaghetti eaten during a two hour test period is indicative of the appetite of the animal.

When tested in this procedure 1-(2-indanyl)thiourea, a representative of the compounds of the invention, exhibited 70% anorexia when administered orally at 50 mg/kg.

The compounds of general formula (I) in which $R^2$ is hydrogen also exhibit activity against gastric ulcers when tested in experimental animals by a procedure similar to that of Brodie et al., *J. Appl. Physiol.*, 1960, 15, 291–294. The compounds also demonstrate an inhibitory effect against the secretion of gastric juice when tested by the procedure of Shay et al., Gastroenterology, 1954, 906–913.

The invention also provides a pharmaceutical preparation comprising a compound of general formula (I) in which $R^2$ is hydrogen in association with a pharmaceutically acceptable carrier.

Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agent; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating materials as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances, a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example, packeted powders or vials or ampoules. The unit dosage form can be a capsule, cachet or tablet itself, or it can be the appropriate number of any of these in package form. The quantity of active ingredient in a unit dose of composition may be varied or adjusted from about 5 mg. to 500 mg., according to the particular need and the activity of the active ingredient. The invention also includes the compounds in the absence of carrier where the compounds are in unit dosage form. The following Examples illustrate the invention:

EXAMPLE 1

1-Benzoyl-3-(2-indanyl)thiourea

To a stirred solution of ammonium thiocyanate (0.837 g.) in acetone (5 ml.) was added benzoyl chloride (1.406 g.) in acetone (10 ml.). The mixture was refluxed for 5 minutes then 2-aminoindane (1.332 g.) in acetone (10 ml.) was added quickly. Refluxing was continued for 10 minutes and the mixture poured into water (75 ml.) to give an oil which solidified on standing. Recrystallisation from ethanol/water afforded the title compound as pale yellow needles (2.151 g.), m.p. 130°–5° C.

Analysis: Found C, 67.63; H, 5.58; N, 9.24. $C_{17}H_{16}N_2OS.1/4H_2O$ requires: C, 67.86; H, 5.53; N, 9.31%.

EXAMPLE 2

1-(2-Indanyl)thiourea

1-Benzoyl-3-(2-indanyl)thiourea (0.931 g.) and sodium hydroxide (0.500 g.) were refluxed in water (6 ml.) for 10 minutes. The mixture was cooled, extracted into chloroform and the chloroform extracts washed with water, dried ($MgSO_4$) and evaporated to give a white solid. Recrystallisation from ethanol/water afforded the title compound as platelets (0.647 g.), m.p. 155.0° C.

Analysis: Found: C, 61.42; H, 6.31; N, 14.40. $C_{10}H_{12}N_2S$ requires: C, 61.03; H, 6.40; N, 14.24%.

EXAMPLE 3 a. 1-Benzoyl-3-(2-indanyl)-3-methylthiourea is prepared by a process analogous to that described in Example 1 substituting the 2-aminoindane by an equivalent amount of 2-methylaminoindane (J. Org. Chem., 1944, 9, 380–91).

b. Hydrolysis of the product of step (a) by a process analogous to that described in Example 2 gives 1-(2-indanyl)-1-methylthiourea.

EXAMPLE 4 a. 1-Benzoyl-3-(5-chloroindan-2-yl)thiourea is prepared by a process analogous to that described in Example 1 substituting the 2-aminoindane by an equivalent amount of 2-amino-5-chloroindane (U.S. Pat. No. 3,178,478).

b. Hydrolysis of the product of step (a) by a process analogous to that described in Example 2 gives 1-(5-chloroindan-2-yl)thiourea.

EXAMPLE 5 a. 1-Benzoyl-3-(5-methoxyindan-2-yl)thiourea is prepared by a process analogous to that described in Example 1 substituting the 2-aminoindane by an equivalent amount of 2-amino-5-methoxyindane (German Pat. No. 952441).

b. Hydrolysis of the product of step (a) by a process analogous to that described in Example 2 gives 1-(5-methoxyindan-2-yl)thiourea.

I claim:

1. A thiourea of the formula

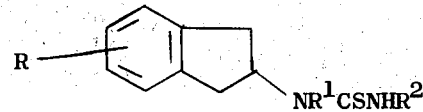

wherein
R is selected from the group consisting of hydrogen, halogen, lower alkyl and lower alkoxy;
$R^1$ is selected from the group consisting of hydrogen and lower alkyl; and
$R^2$ is selected from the group consisting of hydrogen and benzoyl.

2. A thiourea according to claim 1 wherein $R^2$ is hydrogen.

3. A thiourea according to claim 1 which is 1-benzoyl-3-(2-indanyl)thiourea.

4. A thiourea according to claim 1 which is 1-(2-indanyl)thiourea.

5. A pharmaceutical preparation having anorectic activity comprising an anorectically effective amount of a thiourea of the formula

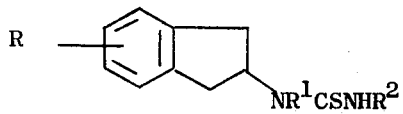

wherein
R is selected from the group consisting of hydrogen, halogen, lower alkyl and lower alkoxy;
$R^1$ is selected from the group consisting of hydrogen and lower alkyl; and
$R^2$ is hydrogen; in association with a pharmaceutically acceptable carrier.

* * * * *